(12) United States Patent
Boesen et al.

(10) Patent No.: US 10,398,374 B2
(45) Date of Patent: *Sep. 3, 2019

(54) MANUAL OPERATION ASSISTANCE WITH EARPIECE WITH 3D SOUND CUES

(71) Applicant: BRAGI GmbH, München (DE)

(72) Inventors: Peter Vincent Boesen, München (DE); Darko Dragicevic, München (DE)

(73) Assignee: BRAGI GmbH, München (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/102,963

(22) Filed: Aug. 14, 2018

(65) Prior Publication Data

US 2019/0000373 A1 Jan. 3, 2019

Related U.S. Application Data

(63) Continuation of application No. 15/803,775, filed on Nov. 4, 2017, now Pat. No. 10,058,282.

(Continued)

(51) Int. Cl.
*A61B 5/00* (2006.01)
*A61B 5/11* (2006.01)
(Continued)

(52) U.S. Cl.
CPC ............ *A61B 5/486* (2013.01); *A61B 5/1124* (2013.01); *A61B 5/6817* (2013.01);
(Continued)

(58) Field of Classification Search
CPC ........ G06F 1/163; G06F 3/167; G06F 9/4411; G06F 9/4446; G09B 9/00; G09B 19/003;
(Continued)

(56) References Cited

U.S. PATENT DOCUMENTS 2,325,590 A 8/1943 Carlisle et al.
2,430,229 A 11/1947 Kelsey
(Continued)

FOREIGN PATENT DOCUMENTS

CN 204244472 U 4/2015
CN 104683519 A 6/2015
(Continued)

OTHER PUBLICATIONS

Stretchgoal—It's Your Dash (Feb. 14, 2014).
(Continued)

*Primary Examiner* — Mohammad K Islam
(74) *Attorney, Agent, or Firm* — Goodhue, Coleman & Owens, P.C.

(57) ABSTRACT

A method of providing audio feedback in response to a user performance using an earpiece includes steps of identifying a manual work operation to be performed by the user, wherein the identifying the manual work operation is performed by the earpiece, monitoring performance of the manual work operation by the user, wherein the monitoring the performance of the work operation is performed by the earpiece, generating 3D sound cues at the earpiece to assist in the performance of the manual work operation by the user, and outputting the 3D sound cues to the user at one or more speakers of the earpiece during the performance of the manual work operation by the user.

13 Claims, 5 Drawing Sheets

Related U.S. Application Data (60) Provisional application No. 62/417,385, filed on Nov. 4, 2016.

(51) Int. Cl.
*H04R 1/10* (2006.01)
*H04R 5/033* (2006.01)

(52) U.S. Cl.
CPC ........... *H04R 1/1016* (2013.01); *H04R 5/033* (2013.01); *A61B 2562/0219* (2013.01); *H04R 2420/07* (2013.01); *H04S 2400/11* (2013.01); *H04S 2420/01* (2013.01)

(58) Field of Classification Search
CPC ......... G09B 19/24; B23P 19/04; G10L 17/02; A61B 2503/20; A61B 2503/24
See application file for complete search history.

(56) References Cited

U.S. PATENT DOCUMENTS

| | | | |
|---|---|---|---|
| 3,047,089 A | 7/1962 | Zwislocki | |
| D208,784 S | 10/1967 | Sanzone | |
| 3,586,794 A | 6/1971 | Michaelis | |
| 3,696,377 A | 10/1972 | Wall | |
| 3,934,100 A | 1/1976 | Harada | |
| 3,983,336 A | 9/1976 | Malek et al. | |
| 4,069,400 A | 1/1978 | Johanson et al. | |
| 4,150,262 A | 4/1979 | Ono | |
| 4,334,315 A | 6/1982 | Ono et al. | |
| D266,271 S | 9/1982 | Johanson et al. | |
| 4,375,016 A | 2/1983 | Harada | |
| 4,588,867 A | 5/1986 | Konomi | |
| 4,617,429 A | 10/1986 | Bellafiore | |
| 4,654,883 A | 3/1987 | Iwata | |
| 4,682,180 A | 7/1987 | Gans | |
| 4,791,673 A | 12/1988 | Schreiber | |
| 4,852,177 A | 7/1989 | Ambrose | |
| 4,865,044 A | 9/1989 | Wallace et al. | |
| 4,984,277 A | 1/1991 | Bisgaard et al. | |
| 5,008,943 A | 4/1991 | Arndt et al. | |
| 5,185,802 A | 2/1993 | Stanton | |
| 5,191,602 A | 3/1993 | Regen et al. | |
| 5,201,007 A | 4/1993 | Ward et al. | |
| 5,201,008 A | 4/1993 | Arndt et al. | |
| D340,286 S | 10/1993 | Seo | |
| 5,280,524 A | 1/1994 | Norris | |
| 5,295,193 A | 3/1994 | Ono | |
| 5,298,692 A | 3/1994 | Ikeda et al. | |
| 5,343,532 A | 8/1994 | Shugart | |
| 5,347,584 A | 9/1994 | Narisawa | |
| 5,363,444 A | 11/1994 | Norris | |
| 5,444,786 A | 8/1995 | Raviv | |
| D367,113 S | 2/1996 | Weeks | |
| 5,497,339 A | 3/1996 | Bernard | |
| 5,606,621 A | 2/1997 | Reiter et al. | |
| 5,613,222 A | 3/1997 | Guenther | |
| 5,654,530 A | 8/1997 | Sauer et al. | |
| 5,689,252 A | 11/1997 | Ayanoglu et al. | |
| 5,692,059 A | 11/1997 | Kruger | |
| 5,721,783 A | 2/1998 | Anderson | |
| 5,748,743 A | 5/1998 | Weeks | |
| 5,749,072 A | 5/1998 | Mazurkiewicz et al. | |
| 5,771,438 A | 6/1998 | Palermo et al. | |
| D397,796 S | 9/1998 | Yabe et al. | |
| 5,802,167 A | 9/1998 | Hong | |
| 5,844,996 A | 12/1998 | Enzmann et al. | |
| D410,008 S | 5/1999 | Almqvist | |
| 5,929,774 A | 7/1999 | Charlton | |
| 5,933,506 A | 8/1999 | Aoki et al. | |
| 5,949,896 A | 9/1999 | Nageno et al. | |
| 5,987,146 A | 11/1999 | Pluvinage et al. | |
| 6,021,207 A | 2/2000 | Puthuff et al. | |
| 6,054,989 A | 4/2000 | Robertson et al. | |
| 6,081,724 A | 6/2000 | Wilson | |
| 6,084,526 A | 7/2000 | Blotky et al. | |
| 6,094,492 A | 7/2000 | Boesen | |
| 6,111,569 A | 8/2000 | Brusky et al. | |
| 6,112,103 A | 8/2000 | Puthuff | |
| 6,157,727 A | 12/2000 | Rueda | |
| 6,167,039 A | 12/2000 | Karlsson et al. | |
| 6,181,801 B1 | 1/2001 | Puthuff et al. | |
| 6,185,152 B1 * | 2/2001 | Shen | G01S 3/80 348/E7.079 |
| 6,208,372 B1 | 3/2001 | Barraclough | |
| 6,230,029 B1 | 5/2001 | Yegiazaryan et al. | |
| 6,275,789 B1 | 8/2001 | Moser et al. | |
| 6,339,754 B1 | 1/2002 | Flanagan et al. | |
| D455,835 S | 4/2002 | Anderson et al. | |
| 6,408,081 B1 | 6/2002 | Boesen | |
| 6,424,820 B1 | 7/2002 | Burdick et al. | |
| D464,039 S | 10/2002 | Boesen | |
| 6,470,893 B1 | 10/2002 | Boesen | |
| D468,299 S | 1/2003 | Boesen | |
| D468,300 S | 1/2003 | Boesen | |
| 6,522,266 B1 | 2/2003 | Soehren et al. | |
| 6,542,721 B2 | 4/2003 | Boesen | |
| 6,560,468 B1 | 5/2003 | Boesen | |
| 6,563,301 B2 | 5/2003 | Gventer | |
| 6,654,721 B2 | 11/2003 | Handelman | |
| 6,664,713 B2 | 12/2003 | Boesen | |
| 6,681,176 B2 | 1/2004 | Funk et al. | |
| 6,690,807 B1 | 2/2004 | Meyer | |
| 6,694,180 B1 | 2/2004 | Boesen | |
| 6,718,043 B1 | 4/2004 | Boesen | |
| 6,721,657 B2 | 4/2004 | Ford et al. | |
| 6,738,485 B1 | 5/2004 | Boesen | |
| 6,748,095 B1 | 6/2004 | Goss | |
| 6,754,358 B1 | 6/2004 | Boesen et al. | |
| 6,784,873 B1 | 8/2004 | Boesen et al. | |
| 6,823,195 B1 | 11/2004 | Boesen | |
| 6,852,084 B1 | 2/2005 | Boesen | |
| 6,879,698 B2 | 4/2005 | Boesen | |
| 6,892,082 B2 | 5/2005 | Boesen | |
| 6,920,229 B2 | 7/2005 | Boesen | |
| 6,952,483 B2 | 10/2005 | Boesen et al. | |
| 6,987,986 B2 | 1/2006 | Boesen | |
| 7,010,137 B1 | 3/2006 | Leedom et al. | |
| 7,113,611 B2 | 9/2006 | Leedom et al. | |
| D532,520 S | 11/2006 | Kampmeier et al. | |
| 7,136,282 B1 | 11/2006 | Rebeske | |
| 7,203,331 B2 | 4/2007 | Boesen | |
| 7,209,569 B2 | 4/2007 | Boesen | |
| 7,215,790 B2 | 5/2007 | Boesen et al. | |
| D549,222 S | 8/2007 | Huang | |
| D554,756 S | 11/2007 | Sjursen et al. | |
| 7,403,629 B1 | 7/2008 | Aceti et al. | |
| D579,006 S | 10/2008 | Kim et al. | |
| 7,463,902 B2 | 12/2008 | Boesen | |
| 7,508,411 B2 | 3/2009 | Boesen | |
| 7,532,901 B1 * | 5/2009 | LaFranchise | H04M 1/6066 178/19.04 |
| D601,134 S | 9/2009 | Elabidi et al. | |
| 7,668,652 B2 | 2/2010 | Spencer et al. | |
| 7,825,626 B2 | 11/2010 | Kozisek | |
| 7,859,469 B1 | 12/2010 | Rosener et al. | |
| 7,965,855 B1 | 6/2011 | Ham | |
| 7,979,035 B2 | 7/2011 | Griffin et al. | |
| 7,983,628 B2 | 7/2011 | Boesen | |
| D647,491 S | 10/2011 | Chen et al. | |
| 8,095,188 B2 | 1/2012 | Shi | |
| 8,108,143 B1 | 1/2012 | Tester | |
| 8,140,357 B1 | 3/2012 | Boesen | |
| 8,238,967 B1 | 8/2012 | Arnold et al. | |
| 8,253,589 B2 | 8/2012 | Grimm et al. | |
| D666,581 S | 9/2012 | Perez | |
| 8,300,864 B2 | 10/2012 | Müllenborn et al. | |
| 8,406,448 B2 | 3/2013 | Lin et al. | |
| 8,430,817 B1 | 4/2013 | Al-Ali et al. | |
| 8,436,780 B2 | 5/2013 | Schantz et al. | |
| D687,021 S | 7/2013 | Yuen | |
| 8,679,012 B1 | 3/2014 | Kayyali | |
| 8,719,877 B2 | 5/2014 | VonDoenhoff et al. | |
| 8,774,434 B2 | 7/2014 | Zhao et al. | |

(56) References Cited

U.S. PATENT DOCUMENTS

| | | | |
|---|---|---|---|
| 8,831,266 B1 | 9/2014 | Huang | |
| 8,891,800 B1 | 11/2014 | Shaffer | |
| 8,994,498 B2 | 3/2015 | Agrafioti et al. | |
| D728,107 S | 4/2015 | Martin et al. | |
| 9,013,145 B2 | 4/2015 | Castillo et al. | |
| 9,037,125 B1 | 5/2015 | Kadous | |
| D733,103 S | 6/2015 | Jeong et al. | |
| 9,081,944 B2 | 7/2015 | Camacho et al. | |
| 9,229,227 B2 | 1/2016 | Border et al. | |
| 9,317,241 B2 | 4/2016 | Tranchina | |
| 9,461,403 B2 | 10/2016 | Gao et al. | |
| 9,510,159 B1 | 11/2016 | Cuddihy et al. | |
| D773,439 S | 12/2016 | Walker | |
| D775,158 S | 12/2016 | Dong et al. | |
| 9,524,631 B1 | 12/2016 | Agrawal et al. | |
| D777,710 S | 1/2017 | Palmborg et al. | |
| 9,544,689 B2 | 1/2017 | Fisher et al. | |
| D788,079 S | 5/2017 | Son et al. | |
| 9,684,778 B2 | 6/2017 | Tharappel et al. | |
| 9,711,062 B2* | 7/2017 | Ellis | G09B 19/0092 |
| 9,729,979 B2 | 8/2017 | Özden | |
| 9,767,709 B2* | 9/2017 | Ellis | G09B 19/0092 |
| 9,818,005 B2 | 11/2017 | Yeager et al. | |
| 9,821,767 B2 | 11/2017 | Nixon | |
| 9,848,257 B2 | 12/2017 | Ambrose et al. | |
| 2001/0005197 A1 | 6/2001 | Mishra et al. | |
| 2001/0027121 A1 | 10/2001 | Boesen | |
| 2001/0043707 A1 | 11/2001 | Leedom | |
| 2001/0056350 A1 | 12/2001 | Calderone et al. | |
| 2002/0002413 A1 | 1/2002 | Tokue | |
| 2002/0007510 A1 | 1/2002 | Mann | |
| 2002/0010590 A1 | 1/2002 | Lee | |
| 2002/0030637 A1 | 3/2002 | Mann | |
| 2002/0046035 A1 | 4/2002 | Kitahara et al. | |
| 2002/0057810 A1 | 5/2002 | Boesen | |
| 2002/0076073 A1 | 6/2002 | Taenzer et al. | |
| 2002/0118852 A1 | 8/2002 | Boesen | |
| 2003/0002705 A1 | 1/2003 | Boesen | |
| 2003/0065504 A1 | 4/2003 | Kraemer et al. | |
| 2003/0100331 A1 | 5/2003 | Dress et al. | |
| 2003/0104806 A1 | 6/2003 | Ruef et al. | |
| 2003/0115068 A1 | 6/2003 | Boesen | |
| 2003/0125096 A1 | 7/2003 | Boesen | |
| 2003/0218064 A1 | 11/2003 | Conner et al. | |
| 2004/0070564 A1 | 4/2004 | Dawson et al. | |
| 2004/0102931 A1* | 5/2004 | Ellis | A61B 5/1038 |
| | | | 702/188 |
| 2004/0160511 A1 | 8/2004 | Boesen | |
| 2005/0017842 A1 | 1/2005 | Dematteo | |
| 2005/0043056 A1 | 2/2005 | Boesen | |
| 2005/0094839 A1 | 5/2005 | Gwee | |
| 2005/0125320 A1 | 6/2005 | Boesen | |
| 2005/0148883 A1 | 7/2005 | Boesen | |
| 2005/0165663 A1 | 7/2005 | Razumov | |
| 2005/0196009 A1 | 9/2005 | Boesen | |
| 2005/0197063 A1* | 9/2005 | White | A63B 24/0021 |
| | | | 455/41.2 |
| 2005/0212911 A1 | 9/2005 | Marvit et al. | |
| 2005/0251455 A1 | 11/2005 | Boesen | |
| 2005/0266876 A1 | 12/2005 | Boesen | |
| 2006/0029246 A1 | 2/2006 | Boesen | |
| 2006/0073787 A1 | 4/2006 | Lair et al. | |
| 2006/0074671 A1 | 4/2006 | Farmaner et al. | |
| 2006/0074808 A1 | 4/2006 | Boesen | |
| 2006/0166715 A1 | 7/2006 | Engelen et al. | |
| 2006/0166716 A1 | 7/2006 | Seshadri et al. | |
| 2006/0220915 A1 | 10/2006 | Bauer | |
| 2006/0258412 A1 | 11/2006 | Liu | |
| 2007/0102009 A1 | 5/2007 | Wong et al. | |
| 2007/0239225 A1 | 10/2007 | Saringer | |
| 2007/0242834 A1 | 10/2007 | Coutinho et al. | |
| 2007/0247800 A1 | 10/2007 | Smith et al. | |
| 2007/0269785 A1* | 11/2007 | Yamanoi | G05B 19/41805 |
| | | | 434/308 |
| 2008/0013747 A1 | 1/2008 | Tran | |
| 2008/0076972 A1 | 3/2008 | Dorogusker et al. | |
| 2008/0090622 A1 | 4/2008 | Kim et al. | |
| 2008/0102424 A1* | 5/2008 | Holljes | A63B 21/0615 |
| | | | 434/247 |
| 2008/0146890 A1 | 6/2008 | LeBoeuf et al. | |
| 2008/0187163 A1 | 8/2008 | Goldstein et al. | |
| 2008/0215239 A1* | 9/2008 | Lee | G01C 21/3629 |
| | | | 701/441 |
| 2008/0253583 A1 | 10/2008 | Goldstein et al. | |
| 2008/0254780 A1 | 10/2008 | Kuhl et al. | |
| 2008/0255430 A1 | 10/2008 | Alexandersson et al. | |
| 2008/0298606 A1 | 12/2008 | Johnson et al. | |
| 2008/0318518 A1 | 12/2008 | Coutinho et al. | |
| 2009/0003620 A1 | 1/2009 | McKillop et al. | |
| 2009/0008275 A1 | 1/2009 | Ferrari et al. | |
| 2009/0017881 A1 | 1/2009 | Madrigal | |
| 2009/0041313 A1 | 2/2009 | Brown | |
| 2009/0073070 A1 | 3/2009 | Rofougaran | |
| 2009/0097689 A1 | 4/2009 | Prest et al. | |
| 2009/0105548 A1 | 4/2009 | Bart | |
| 2009/0154739 A1 | 6/2009 | Zellner | |
| 2009/0182913 A1 | 7/2009 | Rosenblatt et al. | |
| 2009/0191920 A1 | 7/2009 | Regen et al. | |
| 2009/0226017 A1 | 9/2009 | Abolfathi et al. | |
| 2009/0240947 A1 | 9/2009 | Goyal et al. | |
| 2009/0245559 A1 | 10/2009 | Boltyenkov et al. | |
| 2009/0261114 A1 | 10/2009 | McGuire et al. | |
| 2009/0296968 A1 | 12/2009 | Wu et al. | |
| 2009/0299215 A1 | 12/2009 | Zhang | |
| 2009/0303073 A1 | 12/2009 | Gilling et al. | |
| 2009/0304210 A1 | 12/2009 | Weisman | |
| 2010/0007805 A1 | 1/2010 | Vitito | |
| 2010/0033313 A1 | 2/2010 | Keady et al. | |
| 2010/0075631 A1 | 3/2010 | Black et al. | |
| 2010/0106356 A1 | 4/2010 | Trepagnier et al. | |
| 2010/0166206 A1 | 7/2010 | Macours | |
| 2010/0168075 A1 | 7/2010 | Dahlstrom et al. | |
| 2010/0203831 A1 | 8/2010 | Muth | |
| 2010/0210212 A1 | 8/2010 | Sato | |
| 2010/0285771 A1 | 11/2010 | Peabody | |
| 2010/0290636 A1* | 11/2010 | Mao | H04S 7/304 |
| | | | 381/74 |
| 2010/0320961 A1 | 12/2010 | Castillo et al. | |
| 2011/0018731 A1 | 1/2011 | Linsky et al. | |
| 2011/0103609 A1 | 5/2011 | Pelland et al. | |
| 2011/0137141 A1 | 6/2011 | Razoumov et al. | |
| 2011/0140844 A1 | 6/2011 | McGuire et al. | |
| 2011/0140956 A1 | 6/2011 | Henry et al. | |
| 2011/0239497 A1 | 10/2011 | McGuire et al. | |
| 2011/0286615 A1 | 11/2011 | Diodort et al. | |
| 2011/0293105 A1 | 12/2011 | Arie et al. | |
| 2012/0057740 A1 | 3/2012 | Rosal | |
| 2012/0155670 A1 | 6/2012 | Rutschman | |
| 2012/0159617 A1 | 6/2012 | Wu et al. | |
| 2012/0162891 A1 | 6/2012 | Tranchina et al. | |
| 2012/0163626 A1 | 6/2012 | Booij et al. | |
| 2012/0197737 A1 | 8/2012 | LeBoeuf et al. | |
| 2012/0235883 A1 | 9/2012 | Border et al. | |
| 2012/0309453 A1 | 12/2012 | Maguire | |
| 2013/0106454 A1 | 5/2013 | Liu et al. | |
| 2013/0154826 A1 | 6/2013 | Ratajczyk | |
| 2013/0178967 A1* | 7/2013 | Mentz | G06F 3/16 |
| | | | 700/94 |
| 2013/0200999 A1 | 8/2013 | Spodak et al. | |
| 2013/0204617 A1 | 8/2013 | Kuo et al. | |
| 2013/0293494 A1 | 11/2013 | Reshef | |
| 2013/0316642 A1 | 11/2013 | Newham | |
| 2013/0343585 A1 | 12/2013 | Bennett et al. | |
| 2013/0346168 A1 | 12/2013 | Zhou et al. | |
| 2014/0002357 A1 | 1/2014 | Pombo et al. | |
| 2014/0004912 A1 | 1/2014 | Rajakarunanayake | |
| 2014/0010391 A1 | 1/2014 | Ek et al. | |
| 2014/0014697 A1 | 1/2014 | Schmierer et al. | |
| 2014/0020089 A1 | 1/2014 | Perini, II | |
| 2014/0072136 A1 | 3/2014 | Tenenbaum et al. | |
| 2014/0072146 A1 | 3/2014 | Itkin et al. | |
| 2014/0073429 A1* | 3/2014 | Meneses | H04S 3/004 |
| | | | 463/35 |
| 2014/0079257 A1 | 3/2014 | Ruwe et al. | |

(56) References Cited

U.S. PATENT DOCUMENTS

| | | | |
|---|---|---|---|
| 2014/0106677 A1 | 4/2014 | Altman | |
| 2014/0122116 A1 | 5/2014 | Smythe | |
| 2014/0146973 A1 | 5/2014 | Liu et al. | |
| 2014/0153768 A1 | 6/2014 | Hagen et al. | |
| 2014/0163771 A1 | 6/2014 | Demeniuk | |
| 2014/0185828 A1 | 7/2014 | Helbling | |
| 2014/0219467 A1 | 8/2014 | Kurtz | |
| 2014/0222462 A1 | 8/2014 | Shakil et al. | |
| 2014/0235169 A1 | 8/2014 | Parkinson et al. | |
| 2014/0237518 A1 | 8/2014 | Liu | |
| 2014/0270227 A1 | 9/2014 | Swanson | |
| 2014/0270271 A1 | 9/2014 | Dehe et al. | |
| 2014/0276227 A1 | 9/2014 | Pérez | |
| 2014/0279889 A1 | 9/2014 | Luna | |
| 2014/0310595 A1* | 10/2014 | Acharya | G06F 9/4446 715/706 |
| 2014/0321682 A1 | 10/2014 | Kofod-Hansen et al. | |
| 2014/0335908 A1 | 11/2014 | Krisch et al. | |
| 2014/0348367 A1 | 11/2014 | Vavrus et al. | |
| 2015/0028996 A1 | 1/2015 | Agrafioti et al. | |
| 2015/0035643 A1 | 2/2015 | Kursun | |
| 2015/0036835 A1 | 2/2015 | Chen | |
| 2015/0056584 A1* | 2/2015 | Boulware | B23K 9/173 434/234 |
| 2015/0110587 A1 | 4/2015 | Hori | |
| 2015/0124058 A1 | 5/2015 | Okpeva et al. | |
| 2015/0148989 A1 | 5/2015 | Cooper et al. | |
| 2015/0181356 A1 | 6/2015 | Krystek et al. | |
| 2015/0230022 A1 | 8/2015 | Sakai et al. | |
| 2015/0245127 A1 | 8/2015 | Shaffer | |
| 2015/0256949 A1 | 9/2015 | Vanpoucke et al. | |
| 2015/0264472 A1 | 9/2015 | Aase | |
| 2015/0264501 A1 | 9/2015 | Hu et al. | |
| 2015/0310720 A1 | 10/2015 | Gettings et al. | |
| 2015/0317565 A1 | 11/2015 | Li et al. | |
| 2015/0358751 A1 | 12/2015 | Deng et al. | |
| 2015/0359436 A1 | 12/2015 | Shim et al. | |
| 2015/0364058 A1* | 12/2015 | Lagree | G09B 19/003 434/257 |
| 2015/0373467 A1 | 12/2015 | Gelter | |
| 2015/0373474 A1 | 12/2015 | Kraft et al. | |
| 2015/0379251 A1 | 12/2015 | Komaki | |
| 2016/0033280 A1 | 2/2016 | Moore et al. | |
| 2016/0034249 A1 | 2/2016 | Lee et al. | |
| 2016/0071526 A1 | 3/2016 | Wingate et al. | |
| 2016/0072558 A1 | 3/2016 | Hirsch et al. | |
| 2016/0073189 A1 | 3/2016 | Lindén et al. | |
| 2016/0094550 A1 | 3/2016 | Bradley et al. | |
| 2016/0100262 A1 | 4/2016 | Inagaki | |
| 2016/0119737 A1* | 4/2016 | Mehnert | H04S 7/306 381/310 |
| 2016/0124707 A1* | 5/2016 | Ermilov | H04W 4/02 345/156 |
| 2016/0125892 A1 | 5/2016 | Bowen et al. | |
| 2016/0140870 A1 | 5/2016 | Connor | |
| 2016/0142818 A1 | 5/2016 | Park | |
| 2016/0162259 A1 | 6/2016 | Zhao et al. | |
| 2016/0209691 A1 | 7/2016 | Yang et al. | |
| 2016/0226713 A1 | 8/2016 | Dellinger et al. | |
| 2016/0253994 A1 | 9/2016 | Panchapagesan et al. | |
| 2016/0324478 A1 | 11/2016 | Goldstein | |
| 2016/0352818 A1 | 12/2016 | Han et al. | |
| 2016/0353196 A1 | 12/2016 | Baker et al. | |
| 2016/0360350 A1 | 12/2016 | Watson et al. | |
| 2017/0021257 A1* | 1/2017 | Olsen, II | G06F 3/011 |
| 2017/0046503 A1* | 2/2017 | Cho | G09B 5/02 |
| 2017/0059152 A1 | 3/2017 | Hirsch et al. | |
| 2017/0060262 A1 | 3/2017 | Hviid et al. | |
| 2017/0060269 A1 | 3/2017 | Förstner et al. | |
| 2017/0061751 A1 | 3/2017 | Loermann et al. | |
| 2017/0061817 A1* | 3/2017 | Mettler May | G09B 19/003 |
| 2017/0062913 A1 | 3/2017 | Hirsch et al. | |
| 2017/0064426 A1 | 3/2017 | Hviid | |
| 2017/0064428 A1 | 3/2017 | Hirsch | |
| 2017/0064432 A1 | 3/2017 | Hviid et al. | |
| 2017/0064437 A1 | 3/2017 | Hviid et al. | |
| 2017/0065228 A1 | 3/2017 | Hirano | |
| 2017/0078780 A1 | 3/2017 | Qian et al. | |
| 2017/0078785 A1 | 3/2017 | Qian et al. | |
| 2017/0096065 A1 | 4/2017 | Katsuno et al. | |
| 2017/0100277 A1 | 4/2017 | Ke | |
| 2017/0108918 A1 | 4/2017 | Boesen | |
| 2017/0109131 A1* | 4/2017 | Boesen | G06F 3/012 |
| 2017/0110124 A1 | 4/2017 | Boesen et al. | |
| 2017/0110899 A1 | 4/2017 | Boesen | |
| 2017/0111723 A1 | 4/2017 | Boesen | |
| 2017/0111725 A1 | 4/2017 | Boesen et al. | |
| 2017/0111726 A1 | 4/2017 | Martin et al. | |
| 2017/0111740 A1 | 4/2017 | Hviid et al. | |
| 2017/0119318 A1 | 5/2017 | Shay et al. | |
| 2017/0127168 A1 | 5/2017 | Briggs et al. | |
| 2017/0131094 A1 | 5/2017 | Kulik | |
| 2017/0142511 A1 | 5/2017 | Dennis | |
| 2017/0146801 A1 | 5/2017 | Stempora | |
| 2017/0150920 A1 | 6/2017 | Chang et al. | |
| 2017/0151085 A1 | 6/2017 | Chang et al. | |
| 2017/0151447 A1 | 6/2017 | Boesen | |
| 2017/0151668 A1 | 6/2017 | Boesen | |
| 2017/0151918 A1 | 6/2017 | Boesen | |
| 2017/0151930 A1 | 6/2017 | Boesen | |
| 2017/0151957 A1 | 6/2017 | Boesen | |
| 2017/0151959 A1 | 6/2017 | Boesen | |
| 2017/0153114 A1 | 6/2017 | Boesen | |
| 2017/0153636 A1 | 6/2017 | Boesen | |
| 2017/0154532 A1 | 6/2017 | Boesen | |
| 2017/0155985 A1 | 6/2017 | Boesen | |
| 2017/0155992 A1 | 6/2017 | Perianu et al. | |
| 2017/0155993 A1 | 6/2017 | Boesen | |
| 2017/0155997 A1 | 6/2017 | Boesen | |
| 2017/0155998 A1 | 6/2017 | Boesen | |
| 2017/0156000 A1 | 6/2017 | Boesen | |
| 2017/0164890 A1* | 6/2017 | Leip | A61B 5/486 |
| 2017/0178631 A1 | 6/2017 | Boesen | |
| 2017/0180842 A1 | 6/2017 | Boesen | |
| 2017/0180843 A1 | 6/2017 | Perianu et al. | |
| 2017/0180897 A1 | 6/2017 | Perianu | |
| 2017/0188127 A1 | 6/2017 | Perianu et al. | |
| 2017/0188132 A1 | 6/2017 | Hirsch et al. | |
| 2017/0193978 A1 | 7/2017 | Goldman | |
| 2017/0195829 A1 | 7/2017 | Belverato et al. | |
| 2017/0208393 A1 | 7/2017 | Boesen | |
| 2017/0214987 A1 | 7/2017 | Boesen | |
| 2017/0215016 A1 | 7/2017 | Dohmen et al. | |
| 2017/0230752 A1 | 8/2017 | Dohmen et al. | |
| 2017/0251295 A1 | 8/2017 | Pergament et al. | |
| 2017/0251933 A1 | 9/2017 | Braun et al. | |
| 2017/0257698 A1 | 9/2017 | Boesen et al. | |
| 2017/0258329 A1 | 9/2017 | Marsh | |
| 2017/0263236 A1 | 9/2017 | Boesen et al. | |
| 2017/0263376 A1 | 9/2017 | Verschueren et al. | |
| 2017/0266494 A1* | 9/2017 | Crankson | G06K 9/00342 |
| 2017/0273622 A1 | 9/2017 | Boesen | |
| 2017/0280257 A1 | 9/2017 | Gordon et al. | |
| 2017/0297430 A1 | 10/2017 | Hori et al. | |
| 2017/0301337 A1 | 10/2017 | Golani et al. | |
| 2017/0361213 A1* | 12/2017 | Goslin | A63F 13/20 |
| 2017/0366233 A1 | 12/2017 | Hviid et al. | |
| 2018/0007994 A1 | 1/2018 | Boesen et al. | |
| 2018/0008194 A1 | 1/2018 | Boesen | |
| 2018/0008198 A1 | 1/2018 | Kingscott | |
| 2018/0009447 A1 | 1/2018 | Boesen et al. | |
| 2018/0011006 A1 | 1/2018 | Kingscott | |
| 2018/0011682 A1 | 1/2018 | Milevski et al. | |
| 2018/0011994 A1 | 1/2018 | Boesen | |
| 2018/0012228 A1 | 1/2018 | Milevski et al. | |
| 2018/0013195 A1 | 1/2018 | Hviid et al. | |
| 2018/0014102 A1 | 1/2018 | Hirsch et al. | |
| 2018/0014103 A1 | 1/2018 | Martin et al. | |
| 2018/0014104 A1 | 1/2018 | Boesen et al. | |
| 2018/0014107 A1 | 1/2018 | Razouane et al. | |
| 2018/0014108 A1 | 1/2018 | Dragicevic et al. | |
| 2018/0014109 A1 | 1/2018 | Boesen | |
| 2018/0014113 A1 | 1/2018 | Boesen | |

(56) References Cited

U.S. PATENT DOCUMENTS

| | | |
|---|---|---|
| 2018/0014140 A1 | 1/2018 | Milevski et al. |
| 2018/0014436 A1 | 1/2018 | Milevski |
| 2018/0034951 A1 | 2/2018 | Boesen |
| 2018/0040093 A1 | 2/2018 | Boesen |
| 2018/0042501 A1 | 2/2018 | Adi et al. |
| 2018/0056903 A1 | 3/2018 | Mullett |
| 2018/0063626 A1 | 3/2018 | Pong et al. |

FOREIGN PATENT DOCUMENTS

| | | | |
|---|---|---|---|
| CN | 104837094 A | | 8/2015 |
| EP | 1469659 A1 | | 10/2004 |
| EP | 1017252 A3 | | 5/2006 |
| EP | 2903186 A1 | | 8/2015 |
| GB | 2074817 | | 4/1981 |
| GB | 2508226 A | | 5/2014 |
| JP | 06292195 | | 10/1998 |
| WO | 2008103925 A1 | | 8/2008 |
| WO | 2008113053 A1 | | 9/2008 |
| WO | 2007034371 A3 | | 11/2008 |
| WO | 2011001433 A2 | | 1/2011 |
| WO | 2012071127 A1 | | 5/2012 |
| WO | 2013134956 A1 | | 9/2013 |
| WO | 2014046602 A1 | | 3/2014 |
| WO | 2014043179 A3 | | 7/2014 |
| WO | 2015061633 A2 | | 4/2015 |
| WO | 2015110577 A1 | | 7/2015 |
| WO | 2015110587 A1 | | 7/2015 |
| WO | 2016032990 A1 | | 3/2016 |
| WO | 2016187869 A1 | | 12/2016 |

OTHER PUBLICATIONS

Stretchgoal—The Carrying Case for the Dash (Feb. 12, 2014).
Stretchgoal—Windows Phone Support (Feb. 17, 2014).
The Dash + The Charging Case & The BRAGI News (Feb. 21, 2014).
The Dash—A Word From Our Software, Mechanical and Acoustics Team + An Update (Mar. 11, 2014).
Update From BRAGI—$3,000,000—Yipee (Mar. 22, 2014).
Weisiger; "Conjugated Hyperbilirubinemia", Jan. 5, 2016.
Wertzner et al., "Analysis of fundamental frequency, jitter, shimmer and vocal intensity in children with phonological disorders", V. 71, n.5, 582-588, Sep./Oct. 2005; Brazilian Journal of Othrhinolaryngology.
Wikipedia, "Gamebook", https://en.wikipedia.org/wiki/Gamebook, Sep. 3, 2017, 5 pages.
Wikipedia, "Kinect", "https://en.wikipedia.org/wiki/Kinect", 18 pages, (Sep. 9, 2017).
Wikipedia, "Wii Balance Board", "https://en.wikipedia.org/wiki/Wii_Balance_Board", 3 pages, (Jul. 20, 2017).
Akkermans, "Acoustic Ear Recognition for Person Identification", Automatic Identification Advanced Technologies, 2005 pp. 219-223.
Alzahrani et al: "A Multi-Channel Opto-Electronic Sensor to Accurately Monitor Heart Rate against Motion Artefact during Exercise", Sensors, vol. 15, No. 10, Oct. 12, 2015, pp. 25681-25702, XP055334602, DOI: 10.3390/s151025681 the whole document.
Announcing the $3,333,333 Stretch Goal (Feb. 24, 2014).
Ben Coxworth: "Graphene-based ink could enable low-cost, foldable electronics", "Journal of Physical Chemistry Letters", Northwestern University, (May 22, 2013).
Blain: "World's first graphene speaker already superior to Sennheiser MX400", htt://www.gizmag.com/graphene-speaker-beats-sennheiser-mx400/31660, (Apr. 15, 2014).
BMW, "BMW introduces BMW Connected—The personalized digital assistant", "http://bmwblog.com/2016/01/05/bmw-introduces-bmw-connected-the-personalized-digital-assistant", (Jan. 5, 2016).
BRAGI Is on Facebook (2014).
BRAGI Update—Arrival of Prototype Chassis Parts—More People—Awesomeness (May 13, 2014).
BRAGI Update—Chinese New Year, Design Verification, Charging Case, More People, Timeline(Mar. 6, 2015).
BRAGI Update—First Sleeves From Prototype Tool—Software Development Kit (Jun. 5, 2014).
BRAGI Update—Let's Get Ready to Rumble, A Lot to Be Done Over Christmas (Dec. 22, 2014).
BRAGI Update—Memories From April—Update on Progress (Sep. 16, 2014).
BRAGI Update—Memories from May—Update on Progress—Sweet (Oct. 13, 2014).
BRAGI Update—Memories From One Month Before Kickstarter—Update on Progress (Jul. 10, 2014).
BRAGI Update—Memories From the First Month of Kickstarter—Update on Progress (Aug. 1, 2014).
BRAGI Update—Memories From the Second Month of Kickstarter—Update on Progress (Aug. 22, 2014).
BRAGI Update—New People @BRAGI—Prototypes (Jun. 26, 2014).
BRAGI Update—Office Tour, Tour to China, Tour to CES (Dec. 11, 2014).
BRAGI Update—Status on Wireless, Bits and Pieces, Testing—Oh Yeah, Timeline(Apr. 24, 2015).
BRAGI Update—The App Preview, The Charger, The SDK, BRAGI Funding and Chinese New Year (Feb. 11, 2015).
BRAGI Update—What We Did Over Christmas, Las Vegas & CES (Jan. 19, 2014).
BRAGI Update—Years of Development, Moments of Utter Joy and Finishing What We Started(Jun. 5, 2015).
BRAGI Update—Alpha 5 and Back to China, Backer Day, on Track(May 16, 2015).
BRAGI Update—Beta2 Production and Factory Line(Aug. 20, 2015).
BRAGI Update—Certifications, Production, Ramping Up (Nov. 13, 2015).
BRAGI Update—Developer Units Shipping and Status(Oct. 5, 2015).
BRAGI Update—Developer Units Started Shipping and Status (Oct. 19, 2015).
BRAGI Update—Developer Units, Investment, Story and Status(Nov. 2, 2015).
BRAGI Update—Getting Close(Aug. 6, 2015).
BRAGI Update—On Track, Design Verification, How It Works and What's Next(Jul. 15, 2015).
BRAGI Update—On Track, on Track and Gems Overview (Jun. 24, 2015).
BRAGI Update—Status on Wireless, Supply, Timeline and Open House@BRAGI(Apr. 1, 2015).
BRAGI Update—Unpacking Video, Reviews on Audio Perform and Boy Are We Getting Close(Sep. 10, 2015).
Farr, Christina: "iPads in Every Hospital: Apple's Plan to Crack the $3 Trillion Health Care Sector", "https://www.fastcompany.com/3069060/artists-and-scientists-are-teaming-with-businesses-and-non-profits-on-gender-concerns" (Mar. 18, 2017).
Healthcare Risk Management Review, "Nuance updates computer-assisted physician documentation solution" (Oct. 20, 2016).
Hoffman, "How to Use Android Beam to Wirelessly Transfer Content Between Devices", (Feb. 22, 2013).
Hoyt et. al., "Lessons Learned from Implementation of Voice Recognition for Documentation in the Military Electronic Health Record System", The American Health Information Management Association (2017).
Hyundai Motor America, "Hyundai Motor Company Introduces a Health + Mobility Concept for Wellness in Mobility", Fountain Valley, California (2017).
International Search Report & Written Opinion, PCT/EP16/70245 (dated Nov. 16, 2016).
International Search Report & Written Opinion, PCT/EP2016/070231 (dated Nov. 18, 2016).
International Search Report & Written Opinion, PCT/EP2016/070247 (dated Nov. 18, 2016).

(56) References Cited

OTHER PUBLICATIONS

International Search Report & Written Opinion, PCT/EP2016/07216 (dated Oct. 18, 2016).
International Search Report and Written Opinion, PCT/EP2016/070228 (dated Jan. 9, 2017).
Jain A et al: "Score normalization in multimodal biometric systems", Pattern Recognition, Elsevier, GB, vol. 38, No. 12, Dec. 31, 2005, pp. 2270-2285, XP027610849, ISSN: 0031-3203.
Last Push Before the Kickstarter Campaign Ends on Monday 4pm CET (Mar. 28, 2014).
Lovejoy: "Touch ID built into iPhone display one step closer as third-party company announces new tech", "http://9to5mac.com/2015/07/21/virtualhomebutton/" (Jul. 21, 2015).
Nemanja Paunovic et al, "A methodology for testing complex professional electronic systems", Serbian Journal of Electrical Engineering, vol. 9, No. 1, Feb. 1, 2012, pp. 71-80, XP055317584, YU.
Nigel Whitfield: "Fake tape detectors, 'from the stands' footie and UGH? Internet of Things in my set-top box"; http://www.theregisterco.uk/2014/09/24/ibc_round_up_object_audio_dlna.iot/ (Sep. 24, 2014).
Nuance, "ING Netherlands Launches Voice Biometrics Payment System in the Mobile Banking App Powered by Nuance", "https://www.nuance.com/about-us/newsroom/press-releases/ing-netherlands-launches-nuance-voice-biometrics.html", 4 pages (Jul. 28, 2015).
Staab, Wayne J., et al., "A One-Size Disposable Hearing Aid is Introduced", The Hearing Journal 53(4):36-41) Apr. 2000.

\* cited by examiner

MANUAL OPERATION ASSISTANCE WITH EARPIECE WITH 3D SOUND CUES

PRIORITY STATEMENT

This application is a continuation of U.S. patent application Ser. No. 15/803,775, filed Nov. 4, 2017, which claims priority to U.S. Provisional Patent Application No. 62/417,385, filed Nov. 4, 2016, all of which are entitled "Manual Operation Assistance with Earpiece 3D Sound Cues", all of which are hereby incorporated by reference in their entireties.

FIELD OF THE INVENTION

The present invention relates to wearable devices. More particularly, but not exclusively, the present invention relates to earpieces.

BACKGROUND

Real time audio feedback is a concept of potentially great use in many industries today. However, such feedback is not feasible in many instances, either because managers or instructors are too busy with other tasks or electronic devices which may be able to provide such feedback, such as smartphones, may be either too cumbersome or inappropriate for certain tasks. What is needed is a system and method providing audio feedback in response to user performance for manual or prescribed tasks.

SUMMARY

Therefore, it is a primary object, feature, or advantage of the present invention to improve over the state of the art.

It is a further object, feature, or advantage of the present invention to provide audio feedback in response to user performance.

It is a still further object, feature, or advantage of the present invention to monitor user performance such as using detected audio sensed with microphones, movement sensed with inertial sensors, or otherwise.

One or more of these and/or other objects, features, or advantages of the present invention will become apparent from the specification and following claims. No single embodiment need provide every object, feature, or advantage. Different embodiments may have different objects, features, or advantages. Therefore, the present invention is not to be limited to or by an object, feature, or advantage stated herein.

According to one aspect a method of providing audio feedback in response to a user performance using an earpiece includes steps of identifying a manual work operation to be performed by the user, wherein the identifying the manual work operation is performed by the earpiece, monitoring performance of the manual work operation by the user, wherein the monitoring the performance of the work operation is performed by the earpiece, generating 3D sound cues at the earpiece to assist in the performance of the manual work operation by the user, and outputting the 3D sound cues to the user at one or more speakers of the earpiece during the performance of the manual work operation by the user. The 3D sound cues may be generated to be perceived as coming from a spatial location having a contextual relationship with the manual work operation by the user. The monitoring the performance of the manual work operation by the user may be performed by monitoring movement of the user during the manual work operation using one or more inertial sensors of the wireless earpiece. The monitoring the performance of the manual work operation by the user may be performed by monitoring audio of the user sensed by the earpiece during the manual work operation using one or more microphones of the earpiece. The 3D sound cues include voice audio. The manual work operations may be associated with various purposes including therapy such as occupational therapy or physical therapy.

According to another aspect, a method of providing audio feedback in response to a user performance using a set of earpieces including a left ear piece and a right earpiece is provided. The method includes identifying a manual work operation to be performed by the user, wherein the identifying the manual work operation is performed by at least one of the left earpiece and the right earpiece, monitoring performance of the manual work operation by the user, wherein the monitoring the performance of the work operation is performed by the left earpiece and the right earpiece, generating 3D sound cues to assist in the performance of the manual work operation by the user, wherein the generating 3D sound cues is performed at least one of the left earpiece and the right earpiece, and outputting the 3D sound cues to the user at one or more speakers of the left earpiece and one or more speakers of the right earpiece during the performance of the manual work operation by the user. The 3D sound cues may be generated to be perceived as coming from a spatial location having a contextual relationship with the manual work operation by the user. The monitoring the performance of the manual work operation by the user may be performed by monitoring movement of the user during the manual work operation using one or more inertial sensors of the left wireless earpiece and one or more inertial sensors of the right wireless earpiece. The monitoring the performance of the manual work operation by the user may be performed by monitoring audio of the user sensed during the manual work operation using one or more microphones of the left wireless earpiece and one or more microphones of the right wireless earpiece. The monitoring the performance of the manual work operation by the user may be performed by monitoring movement of the user during the manual work operation using one or more inertial sensors of the left wireless earpiece and one or more inertial sensors of the right wireless earpiece and monitoring audio of the user sensed by the earpiece during the manual work operation using one or more microphones of the left wireless earpiece and one or more microphones of the right wireless earpiece.

DETAILED DESCRIPTION

An earpiece or set of earpieces may be used to provide voice feedback to a user and to monitor and track the user's performance of a manual operation or task. The earpiece may assist with the manual operations by providing context-sensitive instructions. For example, where a user is to perform a task with their left hand, audio may be reproduced which sounds as if it is coming from the left of the user through audio processing where a source is appropriately placed. This may be used in any number of different contexts including training for any number of tasks, physical or occupational therapy, sports performance training, or otherwise.

Figure 1:
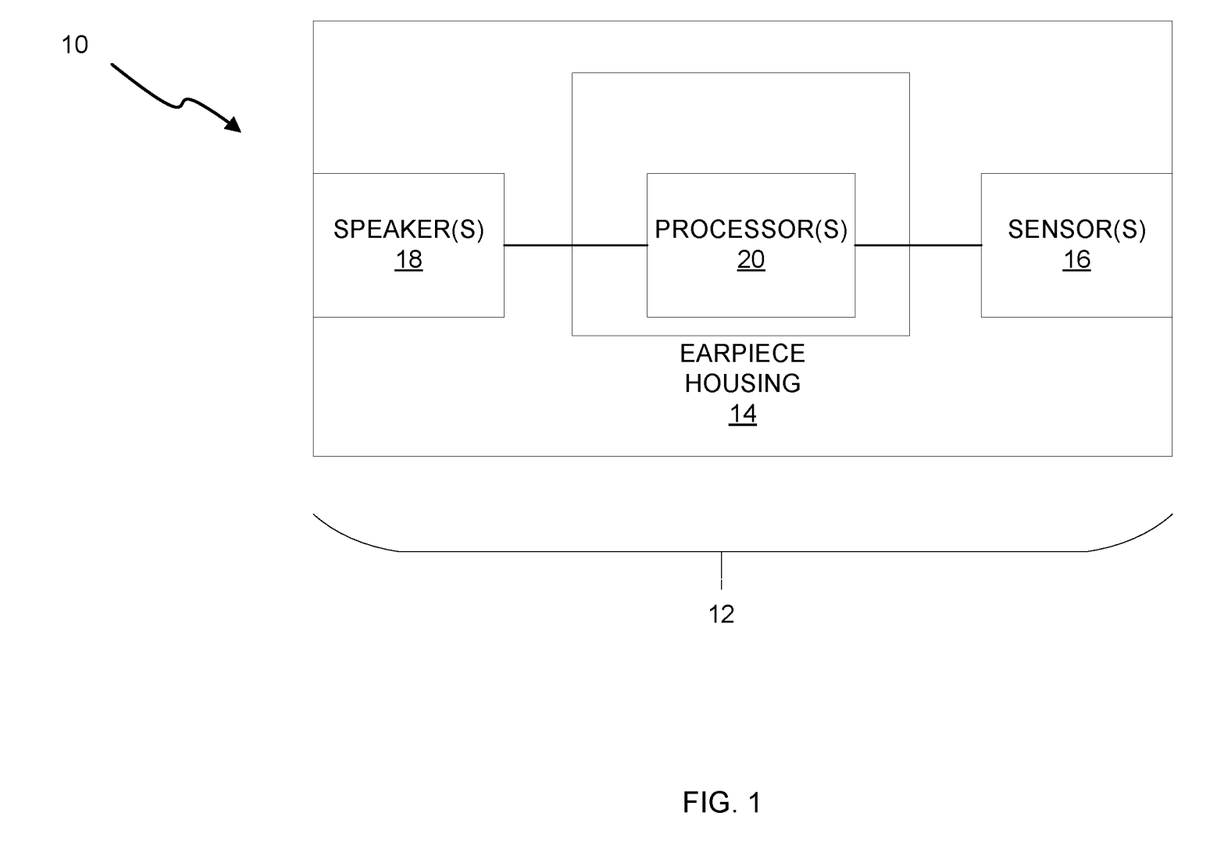
FIG. 1 includes a block diagram of one embodiment of the system

FIG. 1 shows a system 10 which includes an earpiece 12 having an earpiece housing 14, a processor 20 disposed within the earpiece housing 14, at least one sensor 16 operatively connected to the processor 20. The at least one sensor 16 may include an inertial sensor for such as an accelerometer, magnetometer, and/or compass. The sensors 16 may also include one or more microphones. One or more speakers 18 are operatively connected to the processor 20, wherein the processor 20 is configured to produce audio feedback at the speaker 18. The earpiece housing 14 may be composed of soundproof materials or any material resistant to shear and strain and may also have a sheath attached to improve comfort, sound transmission, or reduce the likelihood of skin or ear allergies. In addition, the earpiece housing 14 may also substantially encompass the outer opening of the ear canal of a user to substantially reduce or eliminate external sounds. In addition, the audio feedback or sounds provided by the speaker 18 may be produced in a three-dimensional manner. For example, if the audio feedback relates to poor foot positioning, the audio feedback may be provided in such a manner as the user will interpret the audio feedback as originating from the user's feet to provide additional contextual information. The processor 20 may be further configured to, in addition to producing audio at the speaker 18, process music or sounds stored within a data storage device or received through a radio transceiver, filter and/or process one or more ambient sounds, produce neutralization sound in response to body sounds or other unwanted sounds using destructive interference techniques at the speaker 18. The processor 20 may also produce additional audio feedback in response to one or more user movements sensed by the sensor 16. The user movements prompting the additional audio commands may be preprogrammed or selected by the user or a third party.

Figure 2:
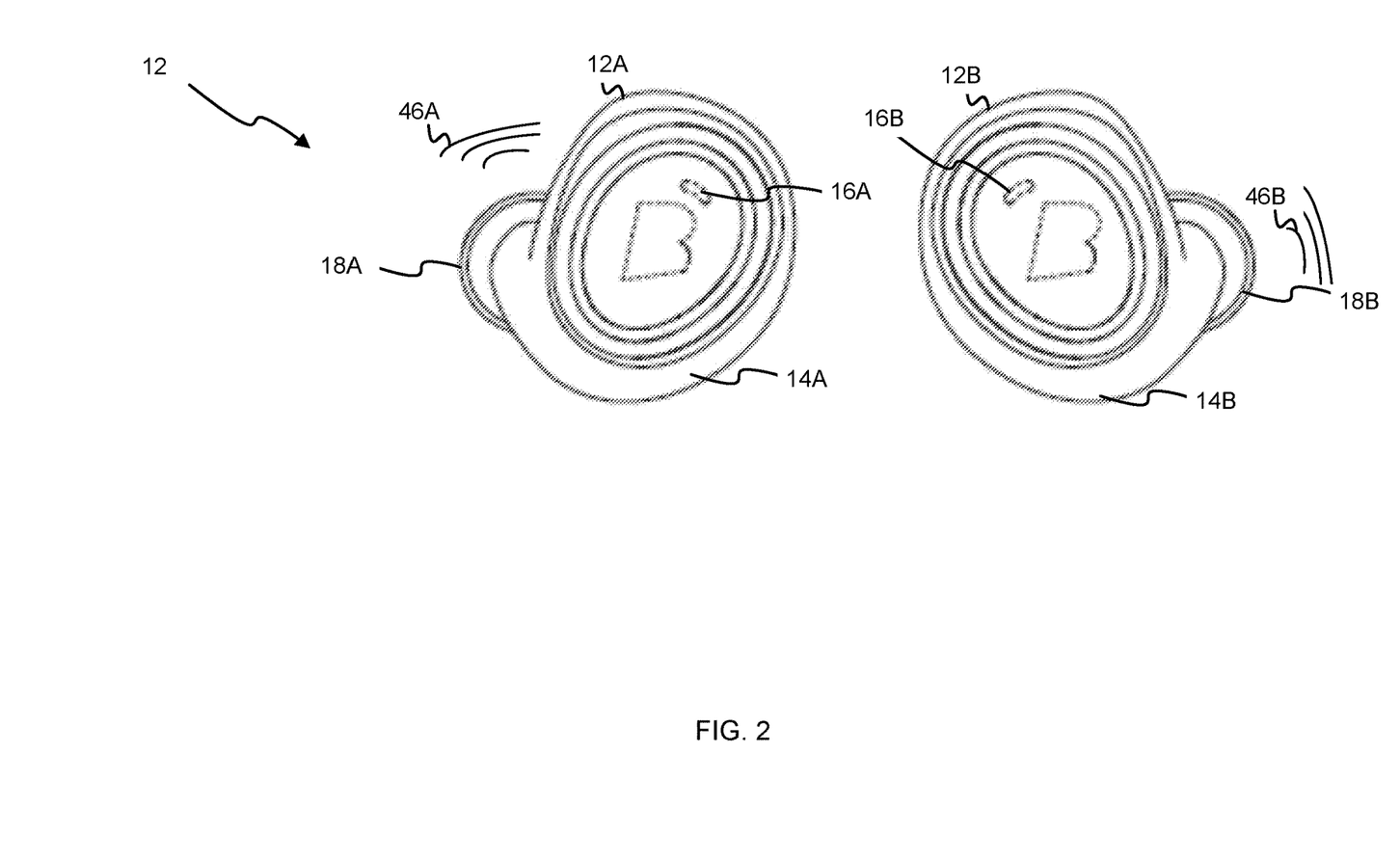
FIG. 2 illustrates the system including the left earpiece and the right earpiece.

FIG. 2 illustrates a pair of earpieces 12 which includes a left wireless earpiece 12A and a right wireless earpiece 12B. The left wireless earpiece 12A has a left earpiece housing 14A. The right wireless earpiece 12B has a right earpiece housing 14B. A sensor 16A is shown on the left earpiece 12A and a sensor 16B is shown on the right earpiece 12B. The sensors 16A and 16B may be located anywhere on the left earpiece 12A and the right earpiece 12B respectively and each sensor may be configured to sense motion of the user. The processor may map the user motion to performance of a manual operation. For example, movements or motions as determined by one or more accelerometers or other inertial sensors may be compared to acceptable movements for performing the manual operations. If detected movements or motions are outside of acceptable ranges, then a determination may be as to the feedback to be given. This may include identifying changes a user should make to improve their motions performed in the manual operations. Speakers 18A and 18B may be configured to communicate audio feedback 46A and 46B.

Figure 3:
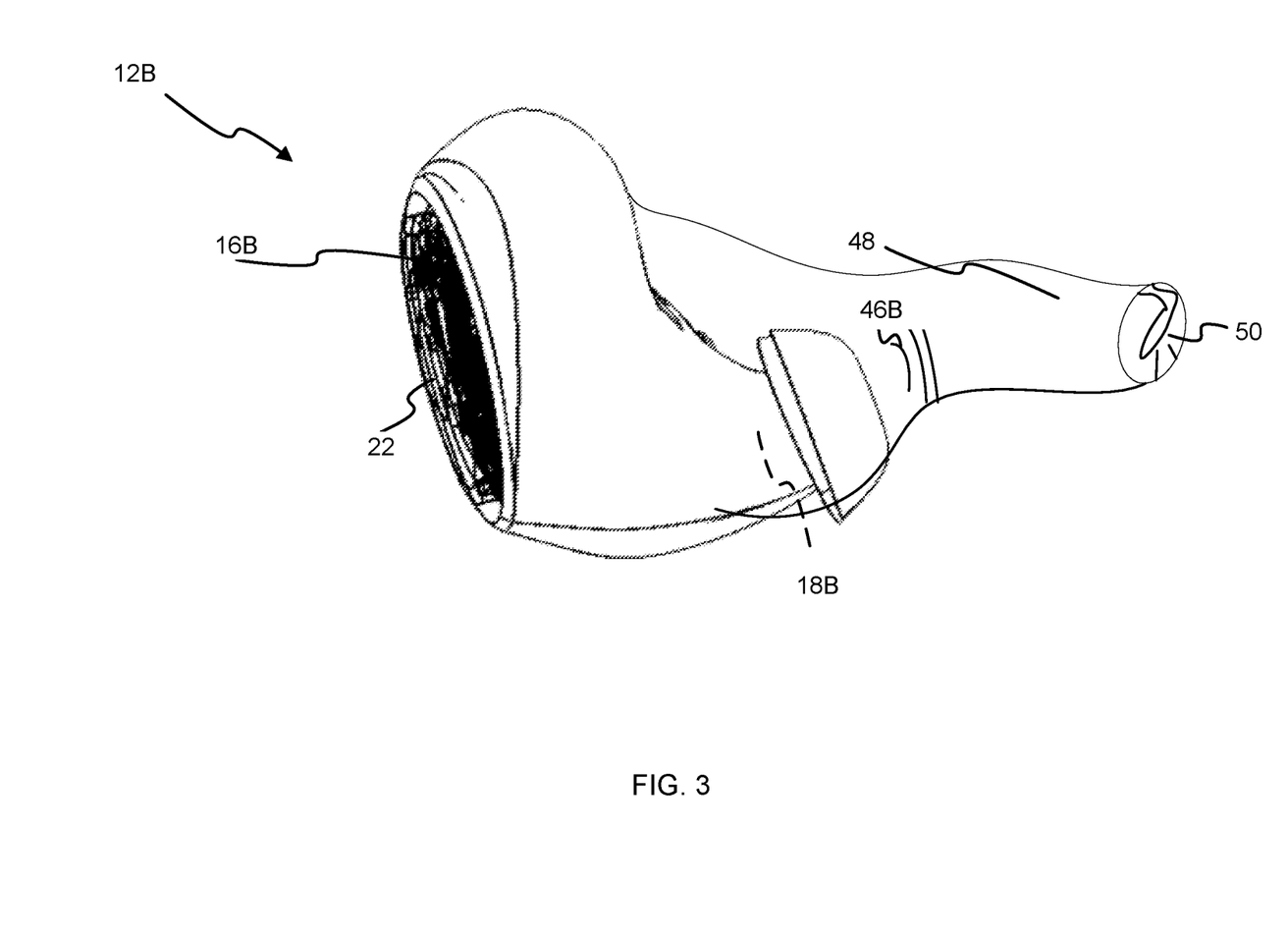
FIG. 3 illustrates the right earpiece and its relationship to a user's ear.

FIG. 3 illustrates a side view of the right earpiece 12B and its relationship to a user's ear. The right earpiece 12B may be configured to minimize the amount of external sound reaching the user's ear canal 48 and/or to facilitate the transmission of the audio feedback 46B from the speaker 18B to a user's tympanic membrane 50. The right earpiece 12B may also be configured to be of any size necessary to comfortably fit within the user's ear canal. A sensor 16B is shown on the exterior of the right earpiece 12B. A gesture control interface 22 is also shown on the exterior of the earpiece and may provide for gesture control by the user or a third party such as by tapping or swiping across the gesture control interface 22, tapping or swiping across another portion of the right earpiece 12B, providing a gesture not involving the touching of the gesture control interface 22 or another part of the right earpiece 12B.

Figure 4:
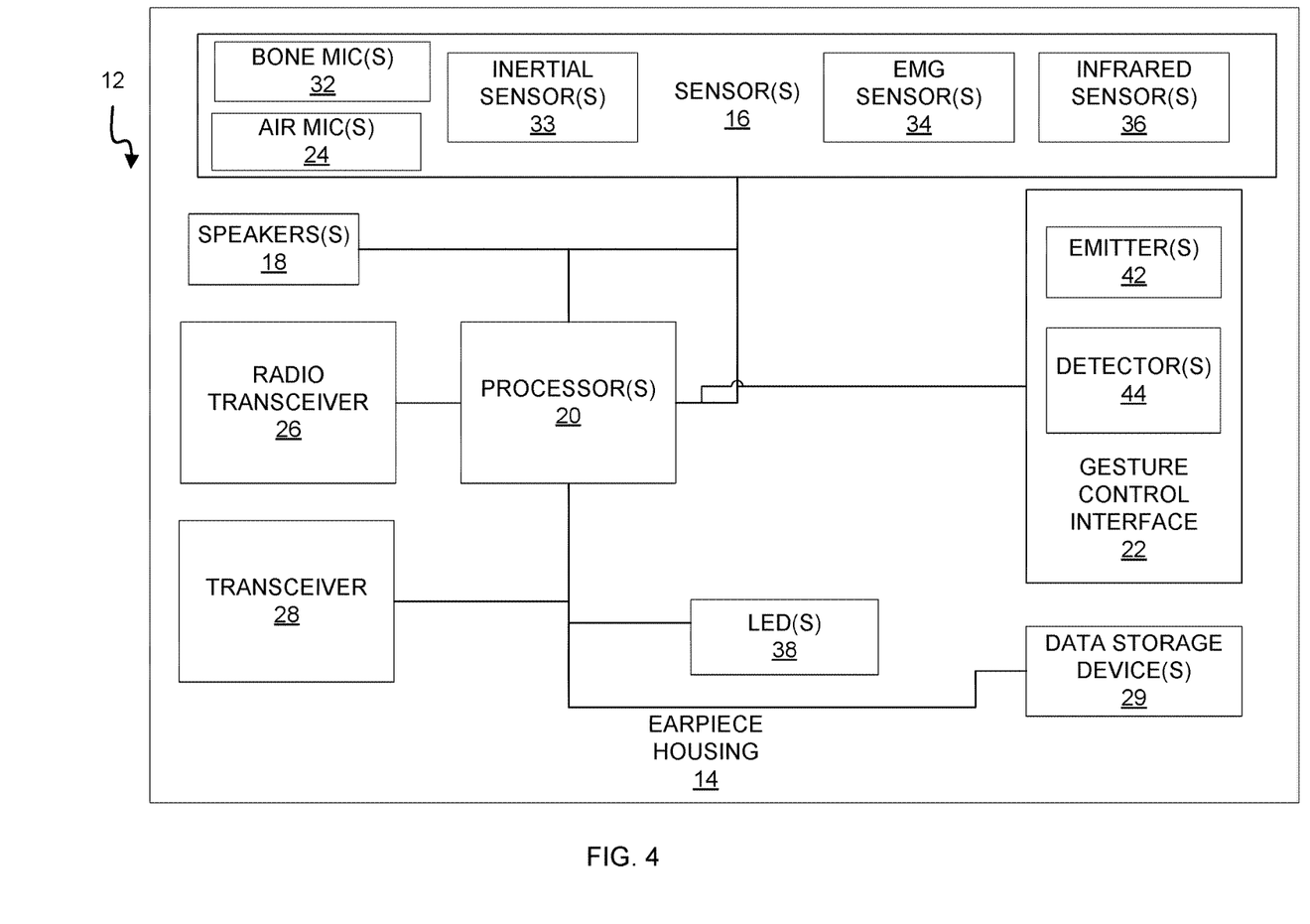
FIG. 4 includes a block diagram of a second embodiment of the system.

FIG. 4 is a block diagram of the system 10 comprising an earpiece 12 having an earpiece housing 14. One or more sensors 16 may be present which are operatively connected to one or more processors 20. The sensors 16 may include one or more bone microphones, one or more air microphones 24, one or more inertial sensors 33, one or more electromyography (EMG) sensors 34, one or more infrared sensors 36, or other types of sensors. Amongst other purposes, the sensors 16 may be used to provide contextual feedback during a user's performance of a work operation.

A processor 20 is disposed within the earpiece housing 14, a gesture control interface 22 with at least one emitter 42 and at least one detector 44 is operatively connected to the one or more processors 20. A radio transceiver 26 disposed within the earpiece housing 14 is also operatively connected to the processor 20. The radio transceiver 26 may be a BLUETOOTH, BLE, Wi-Fi, or other type of radio transceiver. Another transceiver 28 is disposed within the earpiece housing 14 and may be operatively connected to the one or more processors 20. The transceiver 28 may be a magnetic induction transceiver such as a near field magnetic induction (NFMI) transceiver. A data storage device 29 may be disposed within the earpiece housing and operatively connected to the one or more processors 20. The data storage device 29 may store data to be used in analyzing performance of manual operations of the user or in providing audio feedback to the user. One or more LEDs 38 may be operatively connected to the one or more processors 20 to provide visual feedback.

The electromyography (EMG) sensor 34 may be present and configured to read myographic activity from a user to ascertain a facial or other physical gesture and communicate a signal related to the myographic activity to the processor 20. For example, the EMG sensor 34 may sense the electrical activity of a user's facial muscles during a struggle to accomplish a certain task or a problem the user is trying to solve and may submit the resulting readings to the processor 20, which may subsequently produce audio feedback at the speaker 18 to assist the user in fixing or eliminating the problem or alleviating any struggle the user may have. An infrared sensor 36 may also be employed to ascertain the movement of third-party objects or entities. Each sensor 16 may be positioned at any location conducive to receiving information and need not necessarily be in direct contact with either the user or the external environment.

One or more speakers 18 may be operatively connected to the earpiece housing 14 and may be configured to, in addition to producing audio feedback in response to a command from the processor 20, produce one or more ambient and/or non-ambient sounds from one or more microphones 24, 32 or produce one or more audio signals from either the radio transceiver 26, the transceiver 28 or the data storage device 29. The produced sounds may consist of musical sounds, non-musical sounds, commentary, instructions, miscellaneous information, or anything else of interest or importance to the user. In addition, the audio feedback or sounds provided by the speaker 18 may be produced in a three-dimensional manner. For example, if the audio feedback relates to poor foot positioning, the audio feedback may be provided in such a manner as the user or third party will interpret the audio feedback as originating from the user's or third party's feet.

A processor 20 may be disposed within the earpiece housing 14 and operatively connected to components within the earpiece 12 and may be configured to, in addition to producing audio feedback, process signals from the radio transceiver 26, process signals from the transceiver 28, process signals originating from the data storage device 29, process signals from the bone conduction microphone 32, process signals from the EMG sensor 34, process signals from the infrared sensor 36, and process signals from the one or more inertial sensors 33.

A gesture control interface 22 having at least one emitter 42 and a detector 44 may be operatively connected to the one or more processors 20 and may be configured to allow the user or a third party to control one or more functions of the earpiece 12. For example, a menu may be prompted through the use of a gesture with the gestural control interface 22, which may allow the user or a third party to select one or more motions to sense, reprogram or reconfigure the audio feedback to be produced at the speaker 18, listen to a song either stored within the data storage device 29 or received through the radio transceiver 26, listen to a playlist, listen to a newscast or a podcast, listen to a weather report, obtain information on the user's current surroundings, or anything else of interest to the user or a third party, and the aforementioned list is non-exclusive. The selections may be chosen using one or more additional gestures or using one or more voice commands from the user and/or a third party. The types of gestures potentially used with the gesture control interface 22 to control the earpiece 12 include, without limitation, touching, tapping, swiping, use of an instrument, or any combination of the gestures. Touching gestures used to control the earpiece 12 may be of any duration and may include the touching of areas not part of the gesture control interface 22. Tapping gestures used to control the earpiece 12 may include one or more taps and need not be brief. Swiping gestures used to control the earpiece 12 may include a single swipe, a swipe changing direction at least once, a swipe with a time delay, a plurality of swipes, or any combination.

The emitters and detector may be optical emitters and optical detectors. Where optical emitters and detectors are used, additional information may be sensed in addition to gestures of a user. This may include position of the user relative to other objects, or the movement of other objects, or movement of a user in performing a work operation.

One or more microphones 24 may be operatively connected to the earpiece housing 14 and may be configured to receive ambient sounds from one or more outside sources, which may originate from the user, a third party, a machine, an animal, another earpiece, another electronic device, or even nature itself. The ambient sounds received by a microphone 24 may include a word, a combination of words, a sound, a combination of sounds, or any combination. The sounds may be of any frequency and need not necessarily be audible to the user. In addition, one or more microphones 24 may also be configured to receive one or more voice commands which may be used to cease, commence, change, or modify one or more functions of the earpiece 12. For example, a voice command to cease receiving ambient sounds may be provided by the user or a third party saying, "Cease reception of internal ear sounds," or a voice command to play the fifth song in a playlist may be provided by the user or a third party saying, "Play song five in playlist," or "Skip to song five." Other commands may be used to cease, commence, change or modify other functions of the earpiece 12.

A radio transceiver 26 may be disposed within the earpiece 12 and may be configured to receive signals from external electronic devices and to transmit those signals to the processor 20. The external electronic devices the radio transceiver 26 may be configured to receive signals from Bluetooth devices, mobile devices, desktops, laptops, tablets, modems, routers, communications towers, cameras, watches, third-party earpieces, earpieces, other wearable devices, or other electronic devices capable of transmitting or receiving wireless signals. The radio transceiver 26 may receive or transmit more than one signal simultaneously.

A transceiver 28 may be disposed within the earpiece 12 and may be configured to receive signals from and to transmit signals to a second earpiece of the user if the user is using more than one earpiece. The transceiver 28 may receive or transmit more than one signal simultaneously. The transceiver 28 may be of any number of types including a near field magnetic induction (NFMI) transceiver.

One or more LEDs 38 may be operatively connected to the earpiece housing 14 and may be configured to emit light to convey information to a user concerning the earpiece 12. The LEDs 38 may be in any area on the earpiece 12 suitable for viewing by the user or a third party and may consist of as few as one diode which may be provided in combination with a light guide.

Figure 5:
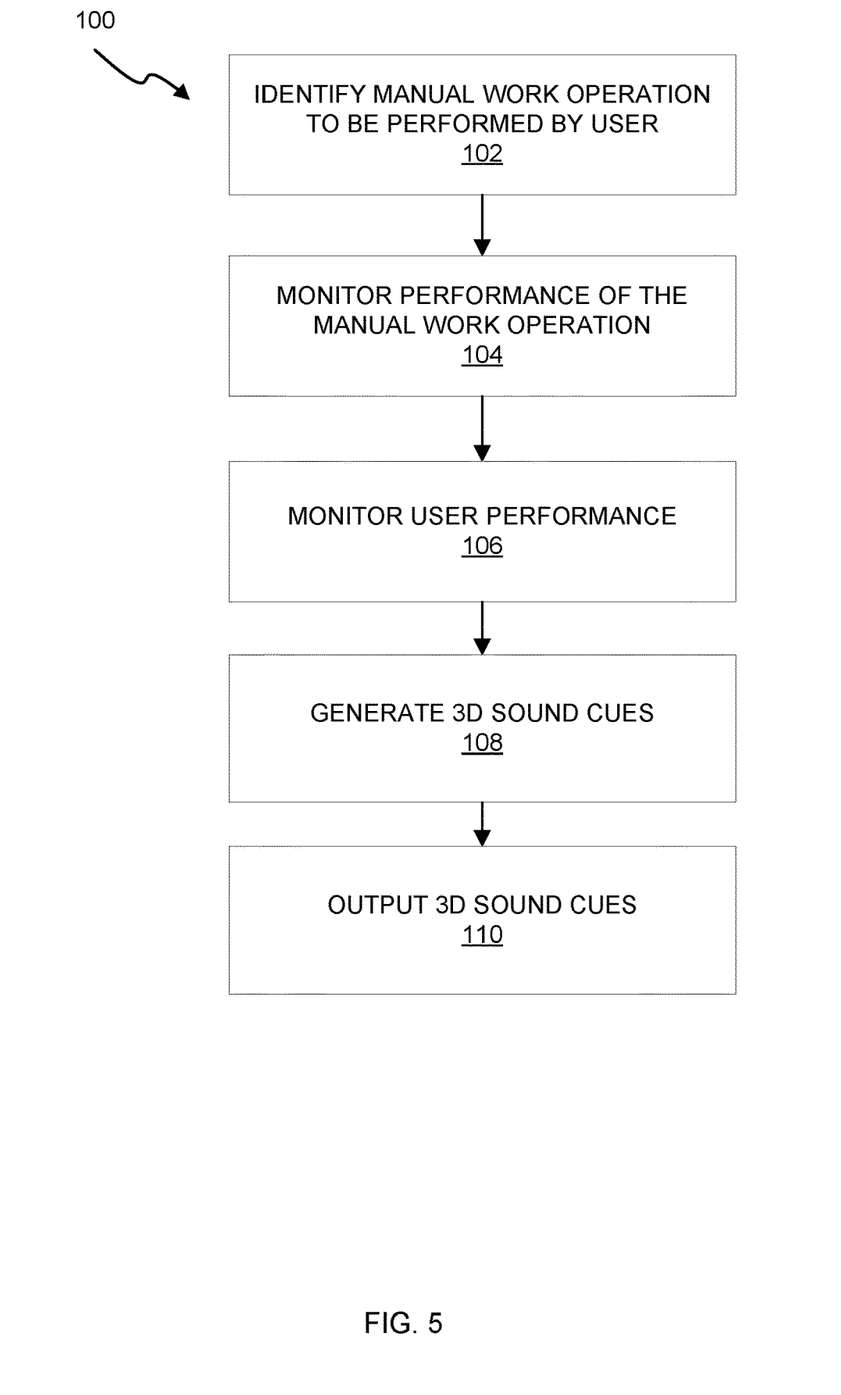
FIG. 5 includes a flowchart of the method of providing voice feedback in response to a user performance using an earpiece.

FIG. 5 illustrates a flowchart of one implementation of the method 100 of providing audio feedback in response to a user performance using an earpiece 100. First, in step 102, a manual work operation to be performed by a user is identified. This identification can occur in several different ways. For example, the user can indicate (s)he is about to perform a manual work operation. This may be accomplished in various ways such as through receiving voice information from the user or by the user using the gestural interface of the earpiece to communicate to the earpiece the user is about to perform a manual work operation. Alternatively, the manual work operation to be performed by a user may be identified using contextual information. Contextual information may include information sensed by the earpiece or any information sensed by or provided by another device in operative communication with the wireless earpiece. This may include ambient audio or motion data, or biometric information sensed by the earpiece or other information such as from a mobile device such as location, or any other information. In step 104, performance of the manual work operation may be monitored. The types of performances a sensor may monitor include a user's physical performance, which may include hand or arm motion, head or foot positioning, or the motion or positioning of another body part of the user or a third party, or the user's or a third party's task performance, which may include, for example, how far to raise a forklift when carrying a specified weight to a given destination, what type of screw to use when constructing a house, the number of heart beats per minute when running, the number of miles remaining when running a specified distance, the number or reps remaining in a given weight-lifting set, or many others. The list is non-exclusive. For example, the earpiece may monitor whether the user's hands are properly aligned when swinging a baseball bat or a golf club, whether the user's feet are properly aligned when throwing a pass, the maximum number of pounds, for example, a forklift can carry and lift without risking harm to either the user or the machine, or how many miles remain for either a specified distance or route when running or jogging. The user monitoring may include external sensors in addition to any sensors operatively connected to the earpiece. The external sensors may be in operative communication with the wireless earpiece through a transceiver of the wireless earpiece. If, in step 106, one or more user performances match one or more conditions necessitating audio feedback, then, in step 108, a processor generates audio feedback which may be in the form of three-dimensional sound cues. In step 110 the 3D sound cues are generated. Three-dimensional sound processing allows for not just audio feedback to a user but also to position the perceived location of the sound cue to provide additional context to the user. For example, if the audio feedback is in the form of an instruction for the user to turn their head slightly to the right during a physical therapy session or occupational therapy session or sports performance training session, then the audio feedback may generate so it is perceived as coming slightly from the right of the user. The audio feedback may be as simple as providing a simple, "Stop" when the user or a third party makes a mistake in either body positioning or task performance or may be more in depth, such as providing specific instructions when a user does not follow the required physical form when performing a task. For example, the earpiece may provide a simple, "Stop" instruction when the user or a third party uses the wrong type of screw when putting something together, or provide detailed instructions concerning the proper mechanics of a golf swing when the user or a third party fails to follow the correct form when swinging a golf club. The audio feedback may also be provided in a three-dimensional manner to assist the user or a third party in following the audio feedback. For example, if the user or a third party has poor foot positioning, the audio feedback may be provided so the user interprets the voice feedback as originating from near the user's or third party's feet, or if the user or third party is improperly executing an instruction, the volume of the voice feedback may be correlated to how far off course the user or third party is regarding the instruction.

It should be understood either a single earpiece may be used or alternatively a set of wireless earpieces may be used. Although the earpieces shown are of an ear bud style configuration, although configurations may be used including headsets.

Therefore, methods, apparatus and system for providing audio feedback in response to a user performance of manual work operations have been shown and described. The present invention contemplates numerous variations, options, and alternatives.

What is claimed is:

1. A method of providing audio feedback in response to a user performance using an earpiece comprising steps of:
   identifying a manual operation to be performed by the user, wherein the identifying the manual operation is performed by the earpiece;
   monitoring performance of the manual operation by the user by mapping movement of the user during the manual work operation as determined using one or more inertial sensors to acceptable movement for performing the manual work operation, wherein the monitoring the performance of the manual operation is performed by the earpiece;
   generating 3D sound cues at the earpiece to assist in the performance of the manual operation by the user;
   outputting the 3D sound cues to the user at one or more speakers of the earpiece during the performance of the manual operation by the user.

2. The method of claim 1 wherein the 3D sound cues are generated to be perceived as coming from a spatial location having a contextual relationship with the manual operation by the user.

3. The method of claim 1 wherein the monitoring the performance of the manual operation by the user is performed by monitoring audio of the user sensed by the earpiece during the manual operation using one or more microphones of the earpiece.

4. The method of claim 1 wherein the monitoring the performance of the manual operation by the user is performed by monitoring movement of the user during the manual operation using one or more inertial sensors of the earpiece and monitoring audio of the user sensed by the earpiece during the manual operation using one or more microphones of the earpiece.

5. The method of claim 1 wherein the 3D sound cues include voice.

6. The method of claim 1 wherein the manual operation is associated with therapy.

7. A method of providing audio feedback in response to a user performance using a set of earpieces including a left ear piece and a right earpiece, the method comprising steps of:
   identifying a manual operation to be performed by the user, wherein the identifying the manual operation is performed by at least one of the left earpiece and the right earpiece;
   monitoring performance of the manual operation by the user by mapping movement of the user during the manual work operation as determined using one or more inertial sensors to acceptable movement for performing the manual work operation, wherein the monitoring the performance of the manual operation is performed by the left earpiece and the right earpiece;
   generating 3D sound cues to assist in the performance of the manual operation by the user, wherein the generating 3D sound cues is performed by at least one of the left earpiece and the right earpiece;
   outputting the 3D sound cues to the user at one or more speakers of the left earpiece and one or more speakers of the right earpiece during the performance of the manual operation by the user.

8. The method of claim 7 wherein the 3D sound cues are generated to be perceived as coming from a spatial location having a contextual relationship with the manual operation by the user.

9. The method of claim 7 wherein the monitoring the performance of the manual operation by the user is performed by monitoring movement of the user during the manual operation using one or more inertial sensors of the left wireless earpiece and one or more inertial sensors of the right wireless earpiece.

10. The method of claim 7 wherein the monitoring the performance of the manual operation by the user is performed by monitoring audio of the user sensed during the manual operation using one or more microphones of the left wireless earpiece and one or more microphones of the right wireless earpiece.

11. The method of claim 7 wherein the monitoring the performance of the manual operation by the user is performed by monitoring movement of the user during the manual operation using one or more inertial sensors of the left wireless earpiece and one or more inertial sensors of the right wireless earpiece and monitoring audio of the user sensed by the earpiece during the manual operation using one or more microphones of the left wireless earpiece and one or more microphones of the right wireless earpiece.

12. The method of claim 7 wherein the 3D sound cues include voice audio.

13. The method of claim 7 wherein the manual operation is associated with therapy.

\* \* \* \* \*